United States Patent
Liao et al.

(10) Patent No.: US 10,524,678 B2
(45) Date of Patent: *Jan. 7, 2020

(54) PHYSIOLOGICAL SIGNAL RECEIVING APPARATUS AND MANUFACTURING METHOD THEREOF

(71) Applicant: Singular Wings Medical Co., Ltd., Hsinchu County (TW)

(72) Inventors: Chin-Chang Liao, Hsinchu County (TW); Chen-Hao Lee, Hsinchu County (TW)

(73) Assignee: Singular Wings Medical Co., Ltd., Hsinchu County (TW)

(*) Notice: Subject to any disclaimer, the term of this patent is extended or adjusted under 35 U.S.C. 154(b) by 361 days.

This patent is subject to a terminal disclaimer.

(21) Appl. No.: 15/595,956

(22) Filed: May 16, 2017

(65) Prior Publication Data

US 2018/0263525 A1    Sep. 20, 2018

(30) Foreign Application Priority Data

Mar. 15, 2017 (TW) .............................. 106108447 A

(51) Int. Cl.
*A61B 5/0408* (2006.01)
*A61B 5/0478* (2006.01)
(Continued)

(52) U.S. Cl.
CPC .......... *A61B 5/0408* (2013.01); *A61B 5/0478* (2013.01); *A61B 5/0492* (2013.01);
(Continued)

(58) Field of Classification Search
CPC ... A61B 5/0408; A61B 5/0478; A61B 5/0492; A61B 5/053
See application file for complete search history.

(56) References Cited

U.S. PATENT DOCUMENTS

| | | | | |
|---|---|---|---|---|
| 4,014,345 A | * | 3/1977 | Kameny | A61N 1/0456 607/152 |
| 4,166,456 A | * | 9/1979 | Wilson | A61B 5/0408 600/392 |

(Continued)

FOREIGN PATENT DOCUMENTS

| | | |
|---|---|---|
| TW | 200520297 | 6/2005 |
| TW | M440760 | 11/2012 |

(Continued)

OTHER PUBLICATIONS

"Office Action of Taiwan Counterpart Application," dated Feb. 2, 2018, p. 1-p. 5, in which the listed references were cited.

*Primary Examiner* — Lee S Cohen
(74) *Attorney, Agent, or Firm* — JCIPRNET

(57) ABSTRACT

A physiological signal receiving apparatus and a manufacturing method thereof are provided. The physiological signal receiving apparatus includes an electrode layer, a protective layer and a conductive structure electrically connected to the electrode layer. The electrode layer is disposed on a substrate. The electrode layer includes a porous gel and a plurality of conductive particles distributed therein. The protective layer is disposed on the substrate and the electrode layer. The protective layer has an opening exposing a portion of the electrode layer. The porous gel is expanded after absorbing liquid, such that a surface of the electrode layer exposed by the opening is higher than a surface of the protective layer.

8 Claims, 2 Drawing Sheets

(51) Int. Cl.
    *A61B 5/0492* (2006.01)
    *A61B 5/053* (2006.01)
    *A61B 5/00* (2006.01)

(52) U.S. Cl.
    CPC ............ *A61B 5/053* (2013.01); *A61B 5/6804* (2013.01); *A61B 5/6843* (2013.01)

(56) References Cited

U.S. PATENT DOCUMENTS

| | | | | |
|---|---|---|---|---|
| 4,282,878 A * | 8/1981 | Novello | ............... | A61B 5/0408 600/391 |
| 5,087,242 A * | 2/1992 | Petelenz | .............. | A61N 1/0436 604/20 |
| 9,008,748 B2 * | 4/2015 | Su | ........................ | A61B 5/0408 600/388 |
| 9,357,942 B2 * | 6/2016 | Nakashima | .......... | A61B 5/0478 |

FOREIGN PATENT DOCUMENTS

| | | |
|---|---|---|
| TW | 201412880 | 4/2014 |
| TW | I502195 | 10/2015 |
| TW | M523433 | 6/2016 |

\* cited by examiner

PHYSIOLOGICAL SIGNAL RECEIVING APPARATUS AND MANUFACTURING METHOD THEREOF

CROSS REFERENCE TO RELATED APPLICATION

This application claims the priority benefit of Taiwan application serial no. 106108447, filed on Mar. 15, 2017. The entirety of the above-mentioned patent application is hereby incorporated by reference herein and made a part of specification.

BACKGROUND OF THE INVENTION

Field of the Invention

The invention relates to a signal receiving apparatus, and particularly relates to a physiological signal receiving apparatus.

Description of Related Art

For the current human body signal measuring device, an electrode is usually in contact with skin of the human body to receive a current emitted from the human body, and then the current is measured and analyzed to monitor the human body condition. To measure the physiological signal of the human body by clothing, the electrode is usually attached to the cloth, so that one of surfaces of the electrode is in contact with the skin. Except for the portion which is in contact with the skin, the rest of the electrode is covered by a protective layer to avoid the electrode to receive noise and short circuit problems. However, since the protective layer has a certain thickness, the surface of the electrode (the surface which is in contact with the skin) exposed by the protective layer will be lower than a surface of the protective layer. Therefore, the problem that the electrode can not be effectively in contact with the skin or the electrode is easily peeled off after contact with the skin is caused.

SUMMARY OF THE INVENTION

The invention provides a physiological signal receiving apparatus having an electrode layer which is expandable after absorbing liquid.

The invention provides a manufacturing method of a physiological signal receiving apparatus, which can manufacture a physiological signal receiving apparatus having an electrode layer which is expandable after absorbing liquid.

The invention provides a physiological signal receiving apparatus including an electrode layer, a protective layer and a conductive structure electrically connected to the electrode layer. The electrode layer is disposed on a substrate. The electrode layer includes a porous gel and a plurality of conductive particles distributed in the porous gel. The protective layer is disposed on the substrate and the electrode layer. The protective layer has an opening, and the opening exposes a portion of the electrode layer. The porous gel is expanded after absorbing liquid, such that a surface of the electrode layer exposed by the opening is higher than a surface of the protective layer.

According to an embodiment of the invention, the porous gel has a first expansion rate after absorbing the liquid. The substrate has a second expansion rate after absorbing the liquid. The first expansion rate is greater than the second expansion rate.

According to an embodiment of the invention, a material of the porous gel is, for example, polyurethane or silicone resins.

According to an embodiment of the invention, a material of the conductive particles is, for example, at least one selected from the group consisting of metal, carbon black, graphene, and carbon nanotubes.

According to an embodiment of the invention, the liquid is, for example, water and sweat, fat, or a combination thereof generated from the human body.

The invention provides the manufacturing method of the physiological signal receiving apparatus including the following steps. A liquid gel, a plurality of conductive particles and a solvent are mixed to form a slurry. The liquid gel and the solvent are immiscible with each other. The slurry is coated on a substrate. The slurry is cured and the solvent in the slurry is removed to form a porous gel. The porous gel and the conductive particles distributed in the porous gel constitute an electrode layer. A protective layer is formed on the substrate and the electrode layer. The protective layer has an opening, and the opening exposes a portion of the electrode layer. A conductive structure electrically connected to the electrode layer is formed. Additionally, the porous gel is expanded after absorbing liquid, such that a surface of the electrode layer exposed by the opening is higher than a surface of the protective layer.

According to an embodiment of the invention, a material of the liquid gel is polyurethane or silicone resins, for example. The solvent is dimethylformamide or butanone, for example.

According to an embodiment of the invention, a method of removing the solvent in the slurry is to perform a heat treatment or a rinse treatment on the slurry, for example.

According to an embodiment of the invention, the porous gel has a first expansion rate after absorbing the liquid. The substrate has a second expansion rate after absorbing the liquid. The first expansion rate is greater than the second expansion rate.

According to an embodiment of the invention, the liquid is water and sweat, fat, or a combination thereof generated from the human body, for example.

Based on the above, in the invention, the electrode layer has the characteristic of expansion after contacting liquid. The electrode layer may absorb the water before using the physiological signal receiving apparatus, or the electrode layer may be expanded by absorbing the sweat, fat, and other liquids exhausted from the human body after contacting the skin, such that the electrode layer may protrude outwardly from the opening of the protective layer. Therefore, the electrode layer may be effectively in contact with the skin, and will not be easily peeled off from the skin.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
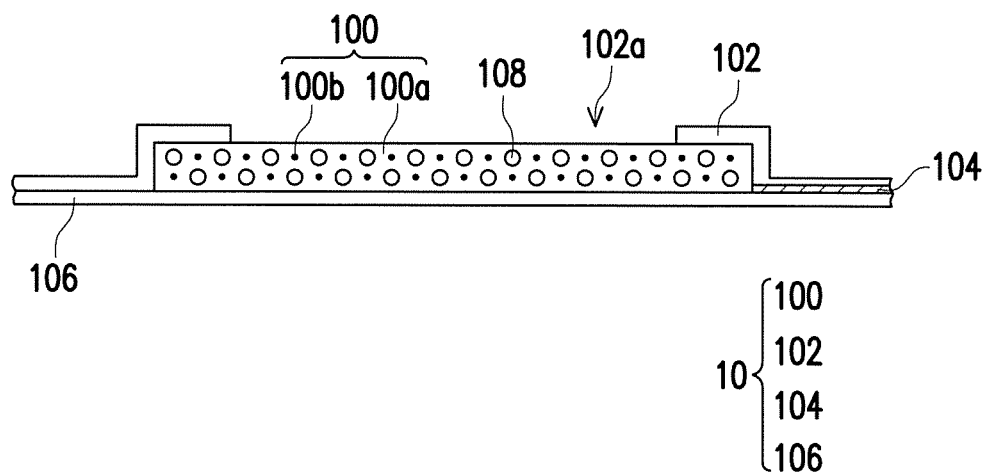
FIG. 1 is a schematic cross-sectional view of a physiological signal receiving apparatus according to an embodiment of the invention.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The physiological signal receiving apparatus of the embodiment can be attached to the living body to receive an electrical signal (e.g., a micro-current emitted from heart, muscle, brain, and so on) emitted from the living body (especially human body), and the aforementioned electrical signal may be measured and analyzed by an external component electrically connected to the physiological signal receiving apparatus of the embodiment to know the condition of the living body.

FIG. 1 is a schematic cross-sectional view of a physiological signal receiving apparatus according to an embodiment of the invention. Referring to FIG. 1, a physiological signal receiving apparatus 10 includes an electrode layer 100, a protective layer 102, a substrate 106, and a conductive structure 104 electrically connected to the electrode layer 100. The physiological signal receiving apparatus 10 may be attached to the living body to receive the electrical signal emitted from the living body by the electrode layer 100. Especially, the micro-current emitted from the heart, muscle, or brain, for example, can be received from the skin by the contact between the electrode layer 100 of the physiological signal receiving apparatus 10 of the embodiment and the skin of the human body.

In the physiological signal receiving apparatus 10, the electrode layer 100 is disposed on the substrate 106. The substrate 106 may be any substrate for carrying the electrode layer 100, the protective layer 102 and the conductive structure 104. In the embodiment, the substrate 106 may be a flexible substrate, such as cloth, a thermoplastic polyurethane (TPU) substrate, or a polyethylene terephthalate (PET) substrate. When the physiological signal receiving apparatus 10 is applied to the so-called "smart clothing" currently, the substrate 106 may be the cloth of the "smart clothing". That is, the physiological signal receiving apparatus 10 may be disposed at an inner surface of the clothing to contact the skin of the human body.

In the embodiment, the electrode layer 100 includes a porous gel 100a and a plurality of conductive particles 100b distributed in the porous gel 100a. The invention does not particularly limit the shape and size of the electrode layer 100. The electrode layer 100 may have various shapes and sizes depending on the actual requirements. A material of the porous gel 100a includes polyurethane or silicone resins. A material of the conductive particles 100b is, for example, at least one selected from the group consisting of metal, carbon black, graphene, and carbon nanotubes. The conductive particles 100b are uniformly distributed in the porous gel 100a, such that the electrode layer 100 can effectively conduct the electrical signal.

Due to the material properties of the porous gel 100a, when the porous gel 100a is in contact with the liquid, it can absorb the liquid. Also, pores 108 of the porous gel 100a may contain the liquid, so that the porous gel 100a may be expanded to increase the volume. In the embodiment, the aforementioned liquid is water and sweat, fat, or a combination thereof generated from the human body, for example. That is, the electrode layer 100 may be expanded to have a greater volume by absorbing the water before using the physiological signal receiving apparatus 10, or the electrode layer 100 may be expanded to have a greater volume by absorbing the sweat, fat, and so on, exhausted from the human body after the electrode layer 100 contacts the skin of the human body.

Figure 2:
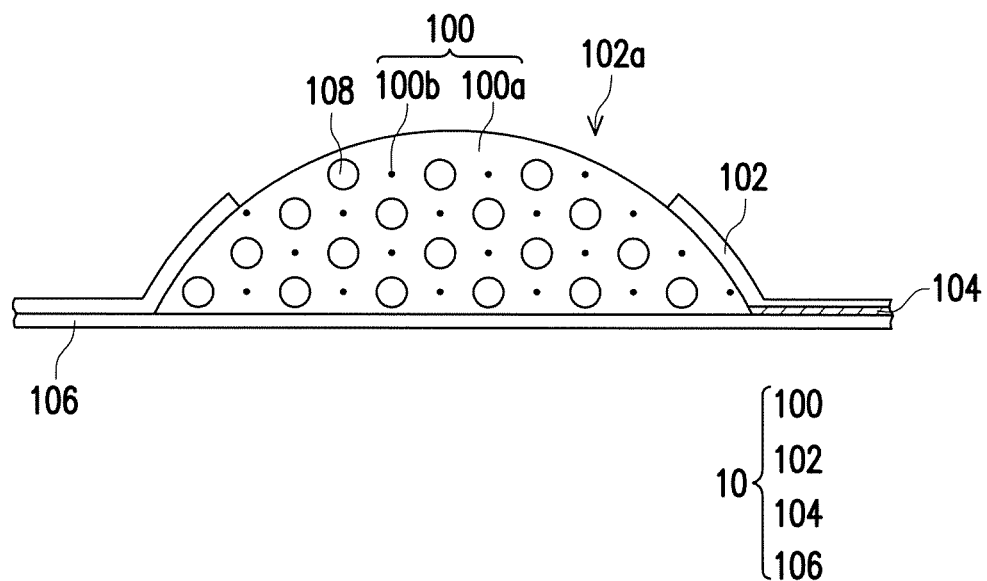
FIG. 2 is a schematic cross-sectional view of a physiological signal receiving apparatus after an electrode layer absorbs a liquid in FIG. 1.

The protective layer 102 is disposed on the substrate 106 and the electrode layer 100. The protective layer 102 has an opening 102a, and the opening 102a exposes a portion of the electrode layer 100. That is, the portion of the electrode layer 100 exposed by the opening 102a is where the physiological signal receiving apparatus 10 is in contact with the human skin. Since the protective layer 102 has a certain thickness (generally, between about 5 μm and 10 mm) to have a protective effect on the electrode layer 100, there is a height difference between a surface of the electrode layer 100 and a surface of the protective layer 102. The height difference will make the electrode layer 100 be difficult to be in contact with the skin, or be easily peeled off after contacting the skin. However, in the embodiment, sine the porous gel 100a has the characteristic of expansion after contacting liquid, the porous gel 100a may be expanded by absorbing the sweat, fat, and other liquids exhausted from the human body after the electrode layer 100 is in contact with the skin. Thus, the electrode layer 100 may protrude outwardly from the opening 102a (i.e., the surface of the electrode layer 100 is higher than the surface of the protective layer 102) as shown in FIG. 2. Therefore, the electrode layer 100 may be effectively in contact with the skin, and will not be easily peeled off from the skin. To ensure that the electrode layer 100 may protrude outwardly from the opening 102a, it is preferred that an expansion rate of the porous gel 100a after absorbing the liquid is greater than an expansion rate of the protective layer 102 after absorbing the liquid. Additionally, it is preferred that the expansion rate of the porous gel 100a after absorbing the liquid is greater than an expansion rate of the substrate 106 after absorbing the liquid, which is also possible to ensure that the electrode layer 100 may protrude outwardly from the opening 102a.

Additionally, since the human body will continue exhausting the sweat, fat and other liquids, the electrode layer 100 may continue absorbing the liquid after contacting the skin. Thus, the physiological signal receiving apparatus 10 will not be easily peeled off from the skin, so as to be attached to the human body for a long time to achieve the purpose of instantly and continuously receiving the electrical signal.

The conductive structure 104 is electrically connected to the electrode layer 100. In the embodiment, the conductive structure 104 may be a wire, and the invention is not limited thereto. One end of the conductive structure 104 is in contact with the electrode layer 100, and another end thereof may be connected to an external device (not shown), so that the electrical signal received by the electrode layer 100 may be conducted to the external device to perform the required treatments. The aforementioned external device may be a signal measuring device, a signal analyzing device, and so on. In the embodiment, the conductive structure 104 is disposed on the substrate 100 and covered by the protective layer 102, but the invention is not limited thereto. In other embodiments, the conductive structure 104 may be disposed at an appropriate position in any manner, as long as it can be electrically connected to the electrode layer 100.

Hereinafter, the manufacturing method of the physiological signal receiving apparatus of the invention will be illustrated by taking the physiological signal receiving apparatus 10 as an example.

Figure 3:
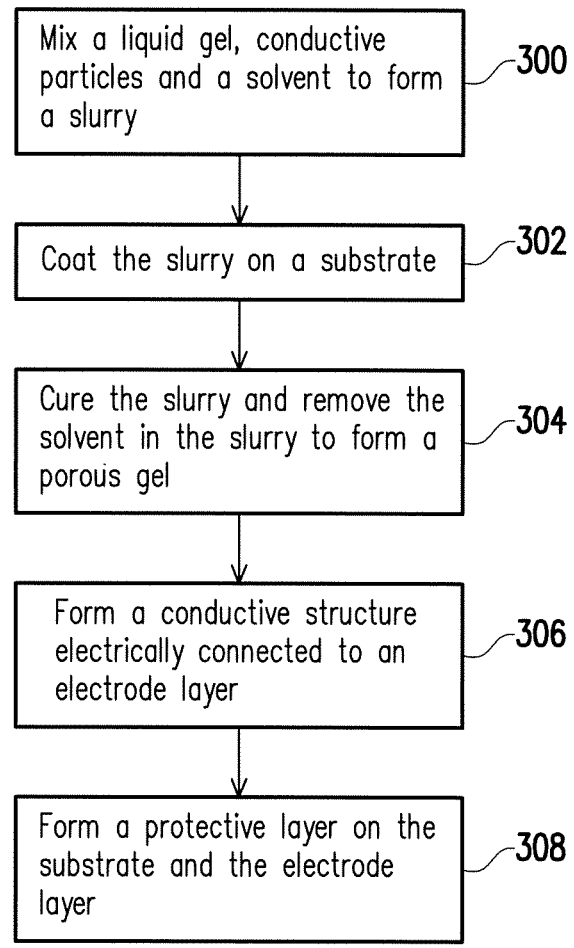
FIG. 3 is a process flow chart of a physiological signal receiving apparatus according to an embodiment of the invention.

FIG. 3 is a process flow chart of the physiological signal receiving apparatus according to an embodiment of the invention. Referring to FIG. 1 and FIG. 3, first, in Step 300, a liquid gel, the conductive particles 100b and the solvent are mixed to form a slurry. The liquid gel is a precursor of the porous gel 100a. The solvent has the property that is immiscible with the liquid gel, and the conductive particles 100b are uniformly distributed in the liquid gel. The solvent is dimethylformamide (DMF) or butanone, for example.

Next, in Step 302, the slurry is coated on the substrate 106. In the embodiment, the slurry may be coated on the substrate 106 by screen printing, a scraper, a roller, and other methods.

Then, in Step 304, the slurry is cured and the solvent in the slurry is removed to form the porous gel 100a. The porous gel 100a and the conductive particles 100b distributed therein constitute the electrode layer 100. The method of curing the slurry may depend on the material of the liquid gel, and the invention is not limited thereto. After the solvent is removed, the space occupied by the original solvent may form the pores 108. A portion of the solvent or all of the solvent may be removed depending on the actual requirements, so as to control the number of the pores 108 in the porous gel 100a. The method of removing the solvent may be to perform a heat treatment (e.g., baking) on the slurry coated on the substrate 106, so that the solvent in the slurry is evaporated. Alternatively, it is also possible to perform a rinse treatment on the slurry coated on the substrate 106, so that the solvent in the slurry is removed.

In the case that the material of the liquid gel is a thermosetting material, the solvent in the slurry may be removed simultaneously in the thermosetting process. Alternatively, after the aforementioned thermosetting, another heat treatment may be performed to remove the solvent in the slurry.

Then, in Step 306, the conductive structure 104 electrically connected to the electrode layer 100 is formed on the substrate 100. The conductive structure 104 is used to electrically connect the physiological signal receiving apparatus 10 to the external device. The conductive structure 104 may be formed in any manner and may be formed in any desired position, and the invention is not limited thereto.

Thereafter, in Step 308, the protective layer 102 with the opening 102a is formed on the substrate 106, the electrode layer 100 and the conductive structure 104, so that a portion of the electrode layer 100 is exposed by the opening 102a, which is used as the portion where the physiological signal receiving apparatus 10 is in contact with the skin to receive the electrical signal.

In the embodiment, after the conductive structure 104 is formed on the substrate 106, the protective layer 102 is formed, but the invention is not limited thereto. In other embodiments, the protective layer 102 may be formed first, and then the conductive structure 104 electrically connected to the electrode layer 100 may be formed at an appropriate region.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A physiological signal receiving apparatus, comprising:
an electrode layer, disposed on a substrate, the electrode layer comprising a porous gel and a plurality of conductive particles distributed in the porous gel;
a protective layer, disposed on the substrate and the electrode layer, wherein the protective layer has an opening, and the opening exposes a portion of the electrode layer; and
a conductive structure, electrically connected to the electrode layer,
wherein the porous gel is expanded after absorbing a liquid, such that a surface of the electrode layer exposed by the opening is higher than a surface of the protective layer.

2. The physiological signal receiving apparatus according to claim 1, wherein the porous gel has a first expansion rate after absorbing the liquid, and the substrate has a second expansion rate after absorbing the liquid, wherein the first expansion rate is greater than the second expansion rate.

3. The physiological signal receiving apparatus according to claim 1, wherein the porous gel is polyurethane or silicone resins.

4. The physiological signal receiving apparatus according to claim 1, wherein the conductive particles are at least one selected from the group consisting of metal, carbon black, graphene, and carbon nanotubes.

5. A manufacturing method of a physiological signal receiving apparatus, comprising:
mixing a liquid gel, a plurality of conductive particles and a solvent to form a slurry, wherein the liquid gel and the solvent are immiscible with each other;
coating the slurry on a substrate;
curing the slurry and removing the solvent in the slurry to form a porous gel, wherein the porous gel and the conductive particles distributed in the porous gel constitute an electrode layer;
forming a protective layer on the substrate and the electrode layer, wherein the protective layer has an opening, and the opening exposes a portion of the electrode layer; and
forming a conductive structure electrically connected to the electrode layer,
wherein the porous gel is expanded after absorbing a liquid, such that a surface of the electrode layer exposed by the opening is higher than a surface of the protective layer.

6. The manufacturing method of the physiological signal receiving apparatus according to claim 5, wherein the liquid gel is polyurethane or silicone resins, and the solvent is dimethylformamide or butanone.

7. The manufacturing method of the physiological signal receiving apparatus according to claim 5, wherein a method of removing the solvent in the slurry comprises performing a heat treatment or a rinse treatment on the slurry.

8. The manufacturing method of the physiological signal receiving apparatus according to claim 5, wherein the porous gel has a first expansion rate after absorbing the liquid, and the substrate has a second expansion rate after absorbing the liquid, wherein the first expansion rate is greater than the second expansion rate.

* * * * *